US009526859B2

(12) United States Patent
Rembrand (10) Patent No.: US 9,526,859 B2
(45) Date of Patent: Dec. 27, 2016

(54) DEVICE METHOD AND SYSTEM FOR REDUCING ANXIETY IN AN INDIVIDUAL

(71) Applicant: BioHug Technologies Ltd, Haifa (IL)

(72) Inventor: Raphael Rembrand, Kiryat Tivon (IL)

(73) Assignee: BIOHUG TECHNOLOGIES, LTD., Haifa (IL)

( * ) Notice: Subject to any disclaimer, the term of this patent is extended or adjusted under 35 U.S.C. 154(b) by 0 days.

(21) Appl. No.: 14/375,794

(22) PCT Filed: Jan. 31, 2013

(86) PCT No.: PCT/IL2013/050092
§ 371 (c)(1),
(2) Date: Jul. 31, 2014

(87) PCT Pub. No.: WO2013/114370
PCT Pub. Date: Aug. 8, 2013

(65) Prior Publication Data
US 2016/0001034 A1    Jan. 7, 2016

(51) Int. Cl.
*A61M 21/00* (2006.01)
*A61M 21/02* (2006.01)
*A61H 9/00* (2006.01)

(52) U.S. Cl.
CPC ............. *A61M 21/02* (2013.01); *A61H 9/0078* (2013.01); *A61H 2201/1418* (2013.01); *A61H 2201/165* (2013.01); *A61H 2201/501* (2013.01); *A61H 2201/5002* (2013.01); *A61H 2201/5097* (2013.01); *A61H 2230/065* (2013.01); *A61H 2230/105* (2013.01); *A61H 2230/305* (2013.01); *A61H 2230/405* (2013.01); *A61H 2230/425* (2013.01); *A61H 2230/505* (2013.01); *A61H 2230/605* (2013.01); *A61H 2230/655* (2013.01); *A61M 2021/0022* (2013.01); *A61M 2205/3303* (2013.01); *A61M 2230/04* (2013.01); *A61M 2230/10* (2013.01); *A61M 2230/40* (2013.01); *A61M 2230/50* (2013.01); *A61M 2230/60* (2013.01)

(58) Field of Classification Search
CPC ........ A61H 9/00; A61H 9/0078; G09B 23/00; G09B 23/28; A61M 21/00
USPC ............................. 600/26–28; 2/69; 434/236
See application file for complete search history.

(56) References Cited

U.S. PATENT DOCUMENTS

| 3,762,396 A | 10/1973 | Ballentine et al. |
| 5,056,505 A | 10/1991 | Warwick et al. |
| 5,291,894 A | 3/1994 | Nagy |

(Continued)

OTHER PUBLICATIONS

Advanced Abnormal Child Psychology/ Edited by Michel Hersen and Robert T. Ammerman p. 62-63.

*Primary Examiner* — John Lacyk
(74) *Attorney, Agent, or Firm* — Edward Langer, Adv. and Patent Attorney (57) ABSTRACT

A system for reducing anxiety in an individual is provided. The system is capable of applying deep pressure to activate a Vegetative Skin Reflex. The system includes a wearable device constructed for covering at least a portion of a body of the individual. The wearable device includes individually expandable units for applying pressure to a specific body region of the individual when expanded and an expandable support unit for expanding and countering the pressure applied to the specific body region by each individual expandable pressure unit.

14 Claims, 6 Drawing Sheets

(56) References Cited

U.S. PATENT DOCUMENTS

| | | | | |
|---|---|---|---|---|
| 5,407,421 | A | * | 4/1995 | Goldsmith .............. A61F 5/012 128/882 |
| 2001/0018563 | A1 | | 8/2001 | Waldridge et al. |
| 2003/0074711 | A1 | * | 4/2003 | Iversen ................. A61H 7/001 2/69 |
| 2005/0273017 | A1 | | 12/2005 | Gordon |
| 2008/0086064 | A1 | * | 4/2008 | Rembrand ........... A61H 9/0078 601/84 |

\* cited by examiner

DEVICE METHOD AND SYSTEM FOR REDUCING ANXIETY IN AN INDIVIDUAL

FIELD AND BACKGROUND OF THE INVENTION

The present invention relates to a device, system and method for reducing anxiety in an individual and, more particularly, to a wearable system capable of applying pressure to selected individual body regions according to physiological feedback and/or preset pressure application sequences.

Individuals suffering from autistic spectrum disorders (ASDs) such as autism and Asperger's syndrome, as well as other behavioral disorders are oftentimes characterized as having sensory abnormalities. In such individuals sensory information (vision, auditory, touch, olfaction, and taste) is sensed normally but perceived abnormally.

Treatment of such individuals attempts to lessen the deficits and abnormal behaviors associated with such disorders, and to increase the quality of life and functional independence of these individuals.

One treatment approach involves a manual application of deep pressure to the body of the individual. Temple Grandin [Journal of Child and Adolescent Psychopharmacology 2 (1) 1992] postulated that deep pressure can serve to organize the central nervous system and modulate the sensory stimuli, and that this in turn leads to a temporary decrease in tactile defensiveness resulting in a decrease in physiological arousal.

Although manual application of deep pressure has been found effective in reducing anxiety most populations, in autistic children it involves human touch, and some elements of control and as such requires a therapist and can raise practicality and strong ethical issues.

Devices for traversing the limitations of manual treatment have been described. Examples of such devices include the Deep Pressure Touch Stimulation (DPTS) vest developed by Brian Mullen at the University of Massachusetts (2008), the vest described in US20030074711 and the vest described by the present inventors in US20080086064.

The above described devices have been found effective in reducing anxiety in autistic children as well as normal individuals, however, they do not address the problem of habituation and effective deep pressure application.

SUMMARY OF THE INVENTION

According to one aspect of the present invention there is provided a system for reducing anxiety in an individual comprising a wearable device constructed for covering at least a portion of a body of the individual, the wearable device including: (a) individually expandable units, each being for applying pressure to a specific body region of the individual when expanded; (b) an expandable support unit being for expanding and countering the pressure applied to the specific body region by each of the individually expandable pressure units, thereby reducing movement of the individually expandable units away from the body when expanded.

According to further features in preferred embodiments of the invention described below, the system further comprises a sensing unit for measuring at least one physiological parameter of the individual.

According to still further features in the described preferred embodiments the system further comprises a control unit for operating each of the individually expandable units and the expandable support unit.

According to still further features in the described preferred embodiments the sensing unit includes at least one sensor selected from the group consisting of a heart rate sensor, a body temperature sensor, a skin moisture sensor, a muscle activity sensor, a blood pressure sensor, a respiratory sensor and a brain activity sensor.

According to still further features in the described preferred embodiments the individually expandable units are fluid expandable reservoirs.

According to still further features in the described preferred embodiments the expandable reservoir unit is a fluid expandable reservoir.

According to still further features in the described preferred embodiments a fluid volume of the expandable reservoir unit is equal to or greater than a combined fluid volume of the individually expandable units.

According to still further features in the described preferred embodiments the wearable device is configured as a vest.

According to still further features in the described preferred embodiment the control unit is capable of operating the individually expandable units at a predetermined sequence of expansion and contraction.

According to still further features in the described preferred embodiment the predetermined sequence is selected by the control unit according to the at least one physiological parameter.

According to still further features in the described preferred embodiments the system further comprises a mechanism for expanding the individually expandable units and the expandable support unit.

According to still further features in the described preferred embodiments the mechanism includes a fluid pump.

According to still further features in the described preferred embodiments the predetermined sequence of expansion and contraction is effected according to the at least one physiological parameter of the individual as measured by the sensing unit According to still further features in the described preferred embodiments the predetermined sequence of expansion and contraction is initiated by the control unit when the at least one physiological parameter remains substantially unchanged over a predetermined time period.

According to another aspect of the present invention there is provided a method of reducing anxiety in an individual comprising: (a) monitoring at least one physiological parameter of the individual to obtain a value of the at least one physiological parameter; (b) applying a first sequence of pressure to selected regions of the body until the value of the at least one physiological parameter changes; and/or (c) applying a second sequence of pressure to selected regions of the body when the value does not substantially change.

According to still further features in the described preferred embodiments the individual suffers from an autistic spectrum disorder.

According to still further features in the described preferred embodiments (a) is effected via a heart rate sensor, a body temperature sensor, a skin moisture sensor, a muscle activity sensor, a blood pressure sensor, a respiratory sensor and/or a brain activity sensor.

According to still further features in the described preferred embodiments (b) is effected using a wearable device having individually expandable units.

According to still further features in the described preferred embodiments the method further comprises repeating (a)-(c) one or more times.

The present invention successfully addresses the shortcomings of the presently known configurations by providing a wearable device that can be used for reducing anxiety in an individual while being devoid of the limitations of prior art devices.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a system which can be used to treat individuals suffering from anxiety and behavioral disorders. Specifically, the present invention can be used to apply pressure to a body of an individual having a Sensory Modulation Disorder (SMD) which is typically present in individuals suffering from Autistic Spectrum Disorders, Rhett's Disorder, Childhood Disintegrative Disorder and the like.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Wearable devices capable of applying pressure to selected body regions of an individual are well known in the art. The present inventors have previously described a vest suitable for such purposes in US20080086064. Use of such devices in reducing the arousal levels of autistic individuals has been documented and is considered a promising treatment option.

While reducing the present invention to practice, the present inventors realized that currently used pressure vests do not adequately address the negative affect of pressure application on the stability of the wearable device on the body and more importantly that such devices do not address habituation which can result from prolonged treatment.

As is further described below, the present invention traverses these problems of prior art devices by providing a wearable device:
(i) Configured for self-stabilization when in use; and/or
(ii) Having sensing and control units capable of identifying and addressing habituation.

Thus, according to one aspect of the present invention there is provided a system for reducing anxiety in an individual. As referred to herein, the term individual" refers to a mammalian subject (e.g. human adult or child) which is suffering from anxiety, stress or a disorder such as trauma or hypertension "Reducing anxiety" in the individual refers to reducing the measurable parameters such as Heart Rate, blood pressure, perspiration, depth of breath, shiftiness, etc.

The system of the present invention includes a wearable device capable of applying pressure to selected regions of the body of the individual when worn and activated. The wearable device can be configured as a vest, shirt, coat or any other configuration (e.g. torso band) capable of applying pressure to selected body regions.

Pressure is activated according to input from sensing (physiological sensors) and control units. As is further described hereinbelow, the control unit is capable of controlling the application of pressure according to sensed physiological parameters and/or preselected pressure application sequences (scripts) which are triggered by physiological sensor data or selected at random.

Such pressure can be applied via mechanical, chemical or fluid-operated expandable units.

For example, a mechanical expandable unit can employ a rotating element shaped as a cam, while a chemical expandable unit can employ chemicals capable of generating gas or foam.

As is further described hereinbelow, a presently preferred embodiment of the wearable device includes expandable units that are expendable via a fluid (gas or liquid) such as air.

Since such expandable units apply pressure to the body of the individual when expanded the force applied by the body on the expandable unit can displace the expandable unit away from the body and reduce the force applied thereby on the body region. A vest or coat configuration tightly bound around the body via straps and the like can counteract such forces and displacement, however, tightly binding the wearable device around the body can also reduce the effect of therapy (pressure application).

To address this problem, the present inventor has devised a wearable device that includes an expandable support unit which is capable of expanding and countering the pressure applied to a specific body region by individual expandable units. Such 'triggered' support reduces movement of the individually expandable units away from the body when expanded.

Such a reservoir serves a second function as a pressure capacitor as is further described below.

Figure 1:
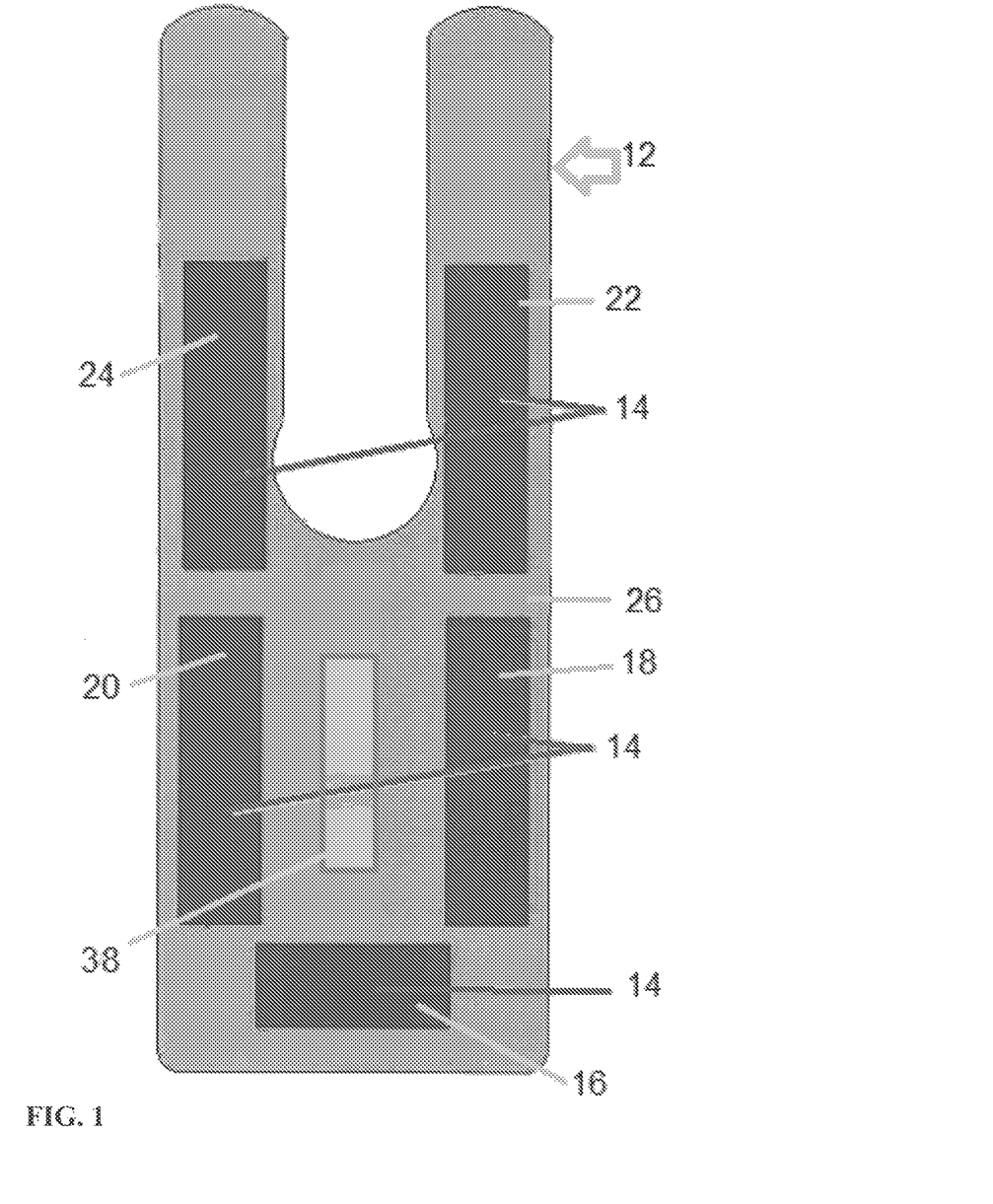
FIG. 1 illustrates the layout of individual pressure units and the pressure reservoir of one embodiment of the present system.
Figure 2:
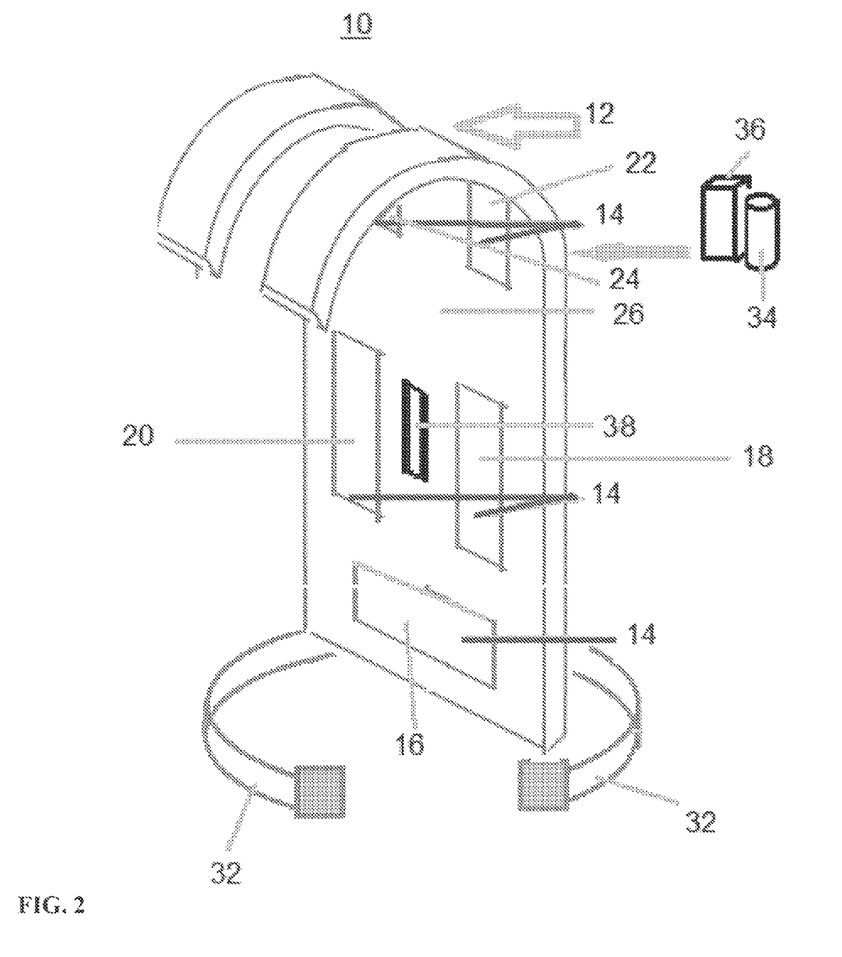
FIG. 2 is the system of FIG. 1 worn on a body of an individual.
Figure 3:
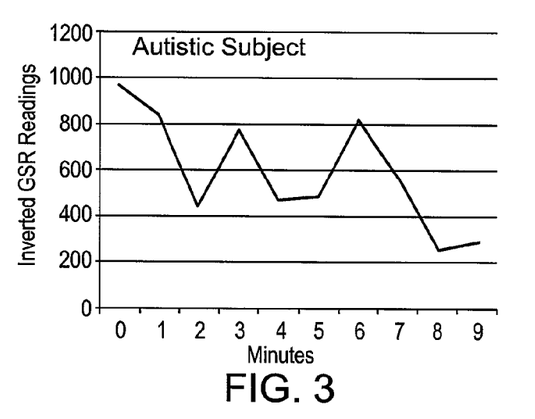
FIGS. 3-11 are graphs illustrating the effect of the present system on the arousal levels of normal and autistic individuals.
Figure 4:
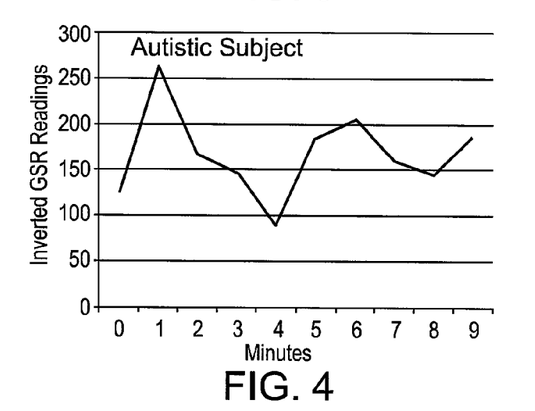
Figure 5:
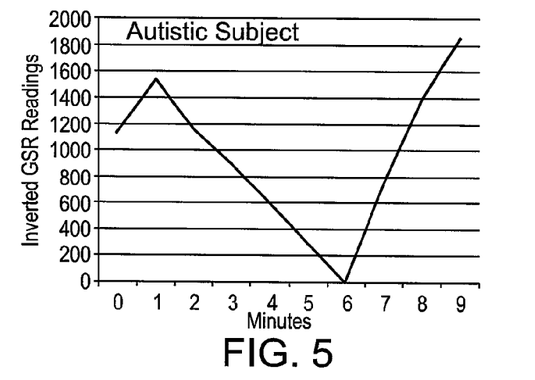
Figure 6:
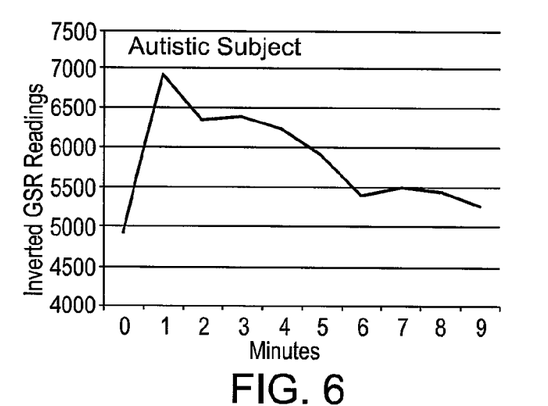
Figure 7:
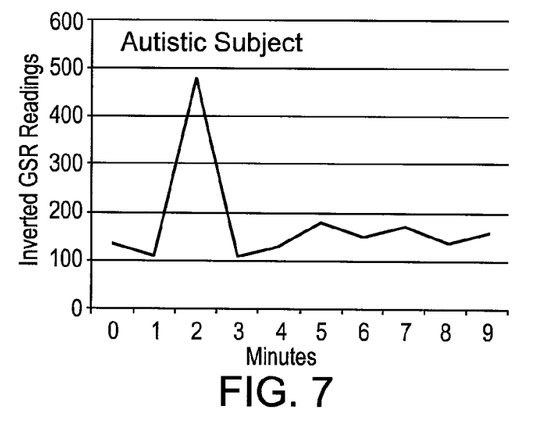
Figure 8:
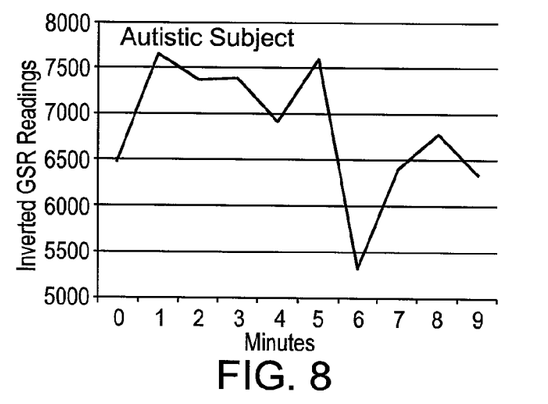
Figure 9:
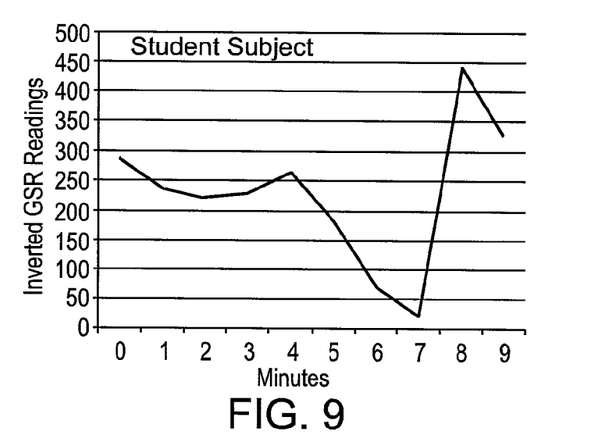
Figure 10:
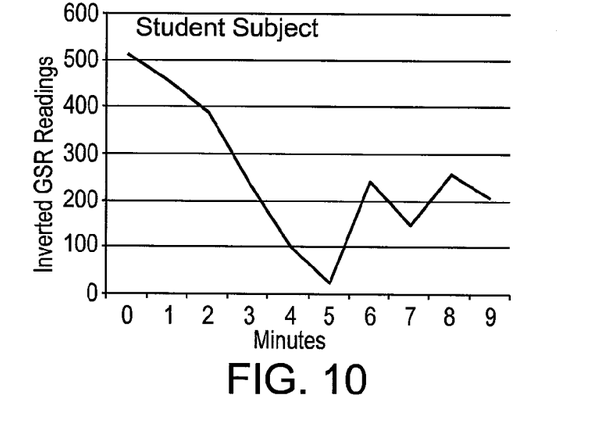

One preferred embodiment of the present system which is referred to herein as system 10 is shown in FIGS. 1-2.

System 10 includes a wearable device 12 which is configured as a vest having one or preferably several (5 shown) individually expandable units 14 which are preferably actuated (inflated/deflated) via a fluid such as air. Units 14 are fabricated from a non- or semi compliant polymer such as PVC and are shaped as flat (substantially two dimensional) squares, rectangles (shown), circles or ovals when empty. When filled with a fluid, expandable units inflate and assume a three dimensional shape that protrudes from a plane defined by the base of each unit 14. The three dimensional shape can have a height of 20-30 cm and a volume of about 1 liter. Units 14 are capable of supporting an internal fluid pressure of up to 0.2-0.5 Bars when filled.

As is shown in FIGS. 1-2, units 14 can be arranged such that they contact the lower back (unit 16), the sides of the back (units 18 and 20) and shoulders/chest (units 22 and 24) of the individual when device 12 is worn thereby.

Wearable device 12 also includes an expandable support unit 26 which serves to counter the pressure applied to a specific body region by unit 16-24. Support unit 26 is fabricated from a non- or semi compliant polymer such as PVC and is shaped as flat (substantially two dimensional) structure when empty. When filled with a fluid, support unit 26 inflates at a regions adjacent to, or around one or more units 16-24 and assume a three dimensional shape. The three dimensional shape can have a height of 40-50 cm and a volume of 3-4 liters. Support unit 26 is capable of supporting an internal fluid pressure of 0.2-0.5 Bars when filled.

In order to counter a normal (to the body region) force produced by any of units 16-24, support unit 26 includes one large inflatable compartment that inflates when the system starts. Inflation of one large inflatable compartment can be used to tightly fasten wearable device 12 to the body and counter act the outward inflation force when units 16-24 are actuated. Such fastening can be effected using a pressure which is high enough to stabilize wearable device 12 on the body when in use.

Wearable device 12 can further include waist straps 32 to further stabilize it on the body of the individual. Waist straps are positioned at a body portion which is not typically subjected to therapeutic pressure and as such would not interfere with treatment. Notwithstanding, a waist strap having individual inflatable units for providing an extra measure of support is also envisaged herein.

The inflatable unit portion of wearable device 12 can be fabricated as a single compartmentalized sheet which can then be covered with a fabric which is provided with fasteners (zippers, Velcro™ straps, buttons etc.) for securing wearable device 12 on the body (preferably torso). The fabric cover can also be used to store additional components of system 10 which are described hereinunder.

Actuation of units 16-24 and support unit 26 is preferably effected using a fluid pump 34 (FIG. 2) such as KOGE KPM32A-12B and a portable power source (battery). Pump 34 is connected to each of units 16-24 and support unit 26 via fluid conduits (e.g. 4-6 mm plastic tubes). Valves positioned at the interface between pump 34 and fluid conduits, along fluid conduits (a valve hub) or between expandable units 16-24 and support unit 26 and fluid conduits control fluid flow.

The fluid conduits and valves enable separate inflation and deflation of each of expandable units 16-24 and support unit 26. Since the volume of support unit 26 is substantially larger than that of each of units 16-24 (can be 2 to 3 times larger), it can also function as a fluid pressure capacitor thereby decreasing the operation cycle of pump 34 and conserving battery power. Support unit 26 can be fluidly connected to each of units 16-24 via a valve hub.

Operation of the valves and pump 34 is controlled by a control unit 36 which is preferably integrated into wearable device or is connected to pump 34 and the valves (valve hub) via wires or wireless communication.

Control unit 36 includes a processing unit for processing information from sensors (further described below) and for providing commands to pump 34 and valves, thereby controlling actuation (inflation/deflation) of units 16-24 and support unit 26. Control unit 36 can include an interface for inputting data (e.g. user data), uploading scripts which set a specific actuation sequence and execute manual control commands from Remote Control Unit.

Control unit can actuate a random or preset sequence (selected by caregiver or individual) of actuation. Such a sequence (termed herein as a script) is a predefined set of instructions, executed by control unit 36 to control the location (as determined by units 16-24) and duration of inflation/deflation over time.

An overly simplified example of such a script can be as follows:

(a) Inflate units 22 and 24 [optionally co-inflate support unit 26]

(b) Wait 3 seconds (c) Inflate units 18 and 20 [optionally co-inflate support unit 26]

(d) Wait 3 seconds (e) Deflate units 22 and 24

Actuation of a script can be used to treat an individual, to prevent habituation or to test the stability of wearable device 12 on the body of the individual and the reaction of the individual to the application of pressure. It can also be used as described to generate repeatable results for comparative research.

Examples of scripts that can be used with the present invention are provided in Example 2 of the Examples section which follows.

Control unit 36 preferably actuates units 16-24 and support unit 26 (i.e. triggers a script) in response to physiological parameter(s) sensed from the individual. Such sensing is effected using one or more sensors 38 including heart rate sensor, a body temperature sensor, a skin moisture sensor (e.g. GSR sensor), a muscle activity sensor, a blood pressure sensor, a respiratory sensor, a brain activity sensor respiratory depth sensor, eye movement sensor.

Sensors 38 can be integrated into wearable device 12 (glued to sheet or fastened to fabric cover) and wired to control unit 36 (e.g. hear rate electrodes) or they can be attached to a body portion (e.g. moisture sensor attached via adhesive patch directly to skin and wired to control unit).

An example of heart rate monitor as used by joggers worn on their chest; this monitor transmits the data wirelessly (using Bluetooth standard) thus enabling the microprocessor to determine if the stress level is increasing (heart rate increasing) or decreasing (heart rate decreasing). An example of a non-physiological measure such as an accelerometer measuring indirectly muscle tonus manifesting itself as weight shifting or muscle tremor; this activity is directly related to stress.

Physiological data monitored by sensors 38 is transmitted to control unit 36 and processed to yield a therapeutic script which activates pump 34 and valves.

There is no absolute value associated with stress, as such, what is monitored is an increase or decrease of physiological values such as a change in pulse count of 10 beats per minute or conductance change of about 500 MHO.

Habituation is the sensory system's mechanism of filtering out constant stimuli to assist in detecting the varying ones. For example, most human beings cease to hear the noise of an air-conditioner in the room after a short time even though the air-conditioner is still working. Another example could be constant deep pressure that does not affect the parasympathetic nervous system after a short time thus rendering an instrument that does not vary the pressure, useless.

Physiological data is also used by the present system to trigger a script designed for preventing habituation (although a habituation-preventing script can also be triggered at random).

For example: when a physiological parameter remains unchanged for several seconds to several minutes, control unit 36, which is programmed to recognize as such situations as potential habituation, triggers pump 34 and valves to apply a sequence of inflation-deflations which are seemingly random but are designed to reduce habituation as described above.

An example of a script which can be used for habituation is provided in Example 2 of the Examples section which follows.

Once the sequence is actuated (one or several times), normal therapeutic actuation signals, such as those described above are triggered by control unit 36.

The present invention can also be configured for remote monitoring via a communication network (e.g. cellular or Internet). By connecting control unit 36 to a communications-capable device such as a cellular telephone (e.g. Smartphone such as the Apple iPhone) or a computer, data collected thereby can be transmitted to a remote server/device for remote monitoring and possibly control.

As is mentioned hereinabove, the present system can be used to treat normal individuals (suffering from anxiety, stress etc) as well as individuals suffering from a disorder such as autism etc.

Thus, according to another aspect of the present invention there is a provided a method of reducing anxiety in an individual. The method is preferably effected using system 10 as follows.

The wearer wears the device and turns it on (the device can also be turned on by a care giver locally or remotely). Two modes of operation can be selected: manual—the user or care giver directly controls the inflation/deflation cycles (open loop); automatic—control unit 36 controls the operation (closed loop). No calibration is needed since treatment goals look for trends in values and not absolute values.

Use of the present device in treating autistic and normal individuals is described in the Examples section which follows.

Thus, the present invention provides a device system and method for reducing anxiety in an individual. The wearable device and system of the present invention is advantageous over known devices in that can be secured to the body of the individual without interfering with therapy and it addresses and corrects habituation which can substantially reduce the effectiveness of treatment over time.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description; illustrate the invention in a non limiting fashion.

Example 1

Human Subject Testing

Deep pressure is frequently used as a method of calming people with a number of disorders, including autism. A study using a prototype of the vest described herein (operated using a repeating, computerized script insure similarity of experience across subjects) was conducted in order to assess the efficacy of the present vest in lowering biometric indicators of stress in people with autism and normal people.

Test Subjects and Procedure: Intervention was performed on 6 subjects with autism and 2 students. Blood pressure readings were collected from 4 autistic subjects. A prototype of the present vest which applies deep pressure to the back, shoulders and sides of the wearer using air pockets that alternatively fill and empty was placed on each subject for a period of about 5 minutes before the mechanism was turned on. The vest was then activated for a period of approximately 10 minutes.

Observation System: Two physiological measures were used for assessing the stress level of the subjects. Blood pressure was measured pre and post intervention using a commercial blood pressure monitor. Continuous readings of Galvanic Skin Response (GSR) were collected using a commercial GSR monitor. Both of these measures are commonly used to assess stress in such devices as lie detectors. Furthermore, GSR has been used in other studies of the efficacy of deep pressure as a calming modality in autistic individuals.

Figure 11:
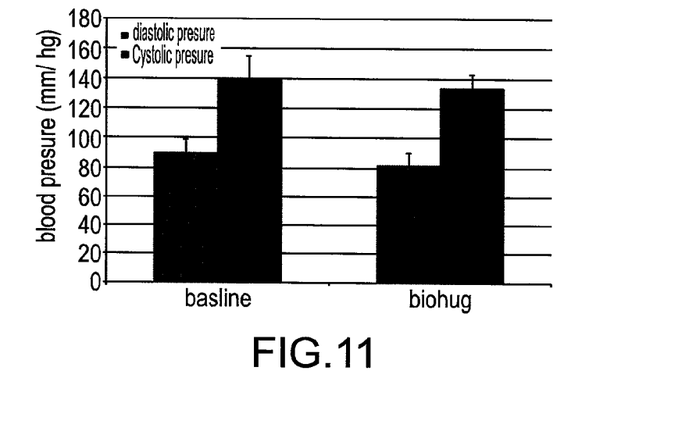
Figure 12:
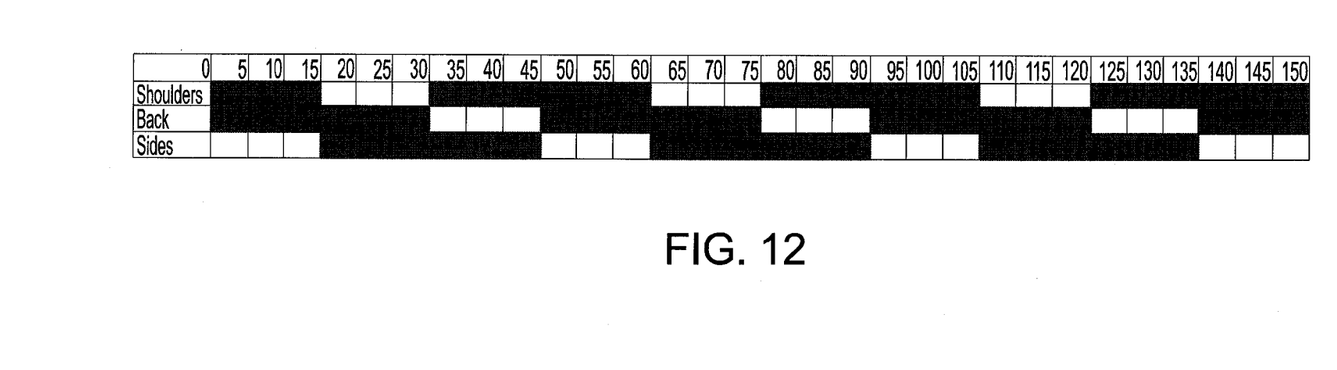
FIG. 12 is a diagram illustrating a simple script; the shaded areas show duration and location of inflation over time.

Results: Subjects with autism tended to experience a brief increase in GSR immediately following the activation of the device (see peak in FIGS. 4, 5, 6, 7, 8). This was followed by a period of increasing relaxation as measured by GSR (downward sloping line in FIGS. 3, 4, 5, 6, 7, 8 9 & 10). The peak of relaxation tended to occur 5 to 6 minutes into the treatment (see FIGS. 5, 6, 8, 10). After 5 or 6 minutes subjects GSR readings tended to increase. Of the subjects from whom blood pressure readings were collected, an average reduction of 10 points was noted in both diastolic and systolic readings (pre-intervention vs. post-intervention, FIG. 11).

Conclusions: As is clearly shown in FIGS. 3-11, use of the present vest produced positive effects on biometric markers for stress across all subjects, regardless of level of functioning or diagnosis.

Example 2

Actuation Script

An example of a script used for calming and avoidance of habituation is described below and shown in FIG. 1. Observations in treated individuals provided several insights into the role of pressure in treatment.

(i) Having at least two sets of expandable units inflated at any given time is beneficial;

(ii) Variation in the pattern of the script can be used to prevent habituation to a repeating set of instructions;

(iii) An inflation command of less than 3 seconds cannot be used due to limitation in speed of inflation; and (iv) Pressure at the shoulders should be first as it usually produces the quickest response.

The following provides examples of typical scripts that can be used with the present invention.

Shoulders 15—Inflate shoulder unit for 15 seconds
Back 30—Inflate back units for 30 seconds
Sides 45—Inflate side units for 45 seconds
Wait 30—Wait before processing further instructions for a random amount of time (greater than 3 Seconds)
Shoulders 30
Wait 15
Back 30
Optionally, repeat 5 times
Wait 15
Sides 30
Wait 15

Further variation can be introduced to prevent habituation to the pattern, for example:

Shoulders 20
Back 35
Wait 20
Sides 30
Wait 15 (may be a conditional wait)
Shoulders 35
Wait 25
Sides 25
Wait 15
Back 25
Wait 20
Shoulders 35
Wait 20
Back 35
Wait 20

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for reducing anxiety in an individual by applying sequences of predetermined pressures and contractions to specific regions of the body of the individual according to sensed physiological parameters associated with anxiety, without causing habituation, said system comprising a wearable device covering at least a portion of a body of the individual, including:
   (a) individually expandable units, each being for applying pressure to a specific body region of the individual when expanded;
   (b) an expandable support unit being for expanding and countering said pressure applied to said specific body region by each of said individually expandable pressure units, thereby reducing movement of said individually expandable units away from said body when expanded;
   c) a mechanism for expanding said individually expandable units and said expandable support unit; and
   d) a control unit capable of operating said individually expandable units in a sequence of expansions and contractions so as to reduce anxiety and avoid habituation.

2. The system of claim 1, further comprising a sensing unit for measuring at least one physiological parameter of the individual.

3. The system of claim 2, wherein said sensing unit includes at least one sensor selected from the group consisting of a heart rate sensor, a body temperature sensor, a skin moisture sensor, a muscle activity sensor, a blood pressure sensor, a respiratory sensor and a brain activity sensor.

4. The control unit of the system of claim 1, wherein the operating of said individually expandable units by said control unit is controlled to reduce anxiety level while avoiding habituation by applying sequences of expansions and contractions determined by physiological parameter data values of the individual monitored by said sensing unit.

5. The system of claim 1, wherein said individually expandable units are fluid expandable reservoirs.

6. The system of claim 5, wherein said expandable support unit is a fluid expandable reservoir.

7. The system of claim 6, wherein a fluid volume of said expandable support unit is equal to or greater than a combined fluid volume of said individually expandable units.

8. The system of claim 1, wherein said wearable device is configured as a vest.

9. The system of claim 1, wherein said mechanism for expanding includes a fluid pump.

10. A method for reducing anxiety in an individual by controlling the application of sequences of predetermined pressures and contractions to specific regions of the body of said individual in accordance to sensed physiological parameters associated with reducing anxiety in an individual, without causing habituation, said method comprising:
   (a) a wearable system having individually expandable units capable of applying pressure by a sequence of expansions and contractions to selected individual body regions, and;
   (b) a control unit capable of operating said individually expandable units in a sequence of expansions and contractions so as to reduce anxiety and avoid habituation.

11. The method of claim 10, wherein said individual suffers from an autism spectrum disorder.

12. The method of claim 10, wherein said at least one habituation preventing sequence of applied pressure by expansions and contractions in which the sequence is predetermined.

13. The method of claim 12, wherein said a wearable system having individually expandable units capable of applying pressure by a sequence of expansions and contractions to selected individual body regions, also includes a sensing unit for monitoring at least one physiological parameter of the individual.

14. The method of claim 13, wherein said at least one habituation preventing sequence of applied pressure by expansions and contractions is triggered by predetermined physiological parameters values of the individual monitored by said sensing unit in claim 9.

* * * * *